United States Patent [19]

Wasson et al.

[11] 4,343,802
[45] Aug. 10, 1982

[54] 2-(3-SUBSTITUTED AMINO-2-HYDROXYPROPOXY)-3-PIPERIDINO PYRAZINES FOR USE IN TREATING HYPERTENSION

[75] Inventors: Burton K. Wasson, Valois, Canada; Leonard M. Weinstock, Belle Mead, N.J.

[73] Assignee: Merck, Sharp & Dohme (I.A.) Corp., Rahway, N.J.

[21] Appl. No.: 165,577

[22] Filed: Jul. 3, 1980

Related U.S. Application Data

[60] Continuation of Ser. No. 861,807, Dec. 19, 1977, abandoned, which is a division of Ser. No. 775,678, Mar. 8, 1977, Pat. No. 4,193,995, which is a division of Ser. No. 584,439, Jun. 6, 1975, Pat. No. 4,042,586, which is a division of Ser. No. 408,032, Oct. 19, 1973, Pat. No. 3,946,009, which is a continuation-in-part of Ser. No. 341,241, Mar. 15, 1973, abandoned.

[51] Int. Cl.$^3$ .................. A61K 31/495; C07D 241/18
[52] U.S. Cl. .................................... 424/250; 544/357
[58] Field of Search .............. 260/243.3; 544/60, 120, 544/357, 405, 408; 424/246, 248, 250

[56] References Cited

U.S. PATENT DOCUMENTS

| | | | |
|---|---|---|---|
| 3,946,009 | 3/1976 | Wasson et al. | 544/405 |
| 4,042,586 | 8/1977 | Wasson et al. | 544/60 |
| 4,193,995 | 3/1980 | Wasson et al. | 544/60 |

*Primary Examiner*—Anton H. Sutto
*Attorney, Agent, or Firm*—Daniel T. Szura; J. Jerome Behan (deceased)

[57] ABSTRACT

2-(3-Substituted amino-2-hydroxypropoxy)-3-substituted pyrazine compounds optionally having substituents in the 5 and/or 6 positions, possessing $\beta$-adrenergic blocking properties are described. The products are prepared by reaction of a 2-chloro (or hydroxy) pyrazine with a 5-hydroxymethyl (or sulfonyloxymethyl) oxazolidine followed by acid hydrolysis.

7 Claims, No Drawings

2-(3-SUBSTITUTED AMINO-2-HYDROXYPROPOXY)-3-PIPERIDINO PYRAZINES FOR USE IN TREATING HYPERTENSION

This is a continuation, of application Ser. No. 861,807, filed, Dec. 19, 1977 now abandoned, which in turn is a division of application Ser. No. 775,678, filed Mar. 8, 1977, now U.S. Pat. No. 4,193,995, which in turn is a division of Ser. No. 584,439, filed June 6, 1975, now U.S. Pat. No. 4,042,586, which in turn is a division of Ser. No. 408,032, filed Oct. 19, 1973, now U.S. Pat. No. 3,946,009 which in turn is a continuation-in-part of Ser. No. 341,241, filed Mar. 15, 1973, now abandoned.

This invention is concerned with 2-(3-substituted amino-2-hydroxypropoxy)-3-substituted pyrazine compounds which can optionally be substituted in the 5 and 6 positions and which exists either in the form of racemic mixtures or as optically active isomers thereof particularly the isomer in the sinister configuration which compounds exhibit β-adrenergic blocking properties.

The novel pyrazine compounds of this invention have the structure

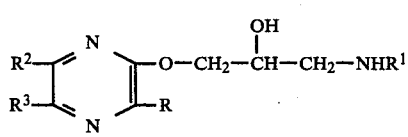

as well as pharmacologically acceptable salts thereof wherein R represents $C_{1-5}$ alkyl, phenyl, substituted phenyl wherein the substituent is $C_{1-3}$alkyl (preferably methyl), $C_{1-3}$alkoxy (preferably methoxy and ethoxy), amino, nitro, or halo (preferably chloro, bromo, or fluoro), phenyl-$C_{1-3}$alkyl, (preferably benzyl), hydroxyphenyl-$C_{1-3}$-alkyl (advantageously hydroxybenzyl), $C_{2-5}$alkoxyalkyl, $C_{5-7}$cycloalkyl, $C_{1-3}$alkoxy, phenoxy, or substituted phenoxy where the substituents are the same as those described above for attachment to the phenyl substituent, benzyloxy optionally having an alkyl, alkoxy, nitro, amino or halo substituent attached to the phenyl moiety of the type described above for attachment to the phenyl substituent, or a 5- to 7- membered N-containing heterocycle which optionally can contain as additional hetero atoms an oxygen, sulfur or one or two additional nitrogen atoms, said N-containing heterocycle advantageously being 1-pyrrolidinyl, piperidino, hexahydroazepinyl, morpholino, thiomorpholino, imidazolyl, pyrazolyl, and triazolyl; $R^1$ represents a straight or branched chain $C_{3-6}$ alkyl, a straight or branched chain hydroxy substituted $C_{3-6}$ alkyl, a straight or branched chain $C_{3-6}$ alkinyl, phenyl-$C_{1-6}$ alkyl or indolyl-$C_{1-6}$ alkyl; $R^2$ and $R^3$ can represent the same or different substituents and represent hydrogen, $C_{1-3}$alkyl, $C_{5-7}$cycloalkyl, $C_{1-3}$alkoxy, phenoxy, phenyl, substituted phenyl wherein the substituents are the same as identified for the phenyl substituents in the definition of varible radical R, amino, acylamino (preferably acetylamino), and a 5- to 7- membered N-containing heterocyclic substituent of the type and variety described in the definition of R substituent, supra.

Suitable pharmacologically acceptable salts of product I are acid addition salts derived from inorganic acids, for example, hydrochlorides, hydrobromides, phosphates, or sulfates or salts derived from organic acids, for example, oxalates, lactates, malates, maleates, formates, acetates, succinates, tartrates, salicylates, citrates, phenylacetates, benzoates, p-toluenesulfonates and other salts such as those that provide relatively insoluble products that afford a slow release of the active material, for example, a 1,1'-methylene-bis(2-hydroxy-3-naphthoate) and the like.

The novel products, I, as well as their intermediates which contain one asymmetric carbon in the propylene chain will be obtained either as a racemic mixture which can be separated into optically active isomers by known methods or the sinister isomer can be directly obtained by use of an appropriate optically active oxazolidine in its sinister configuration. One suitable method for separating the racemic mixture involves formation of a salt thereof with an optically active acid, many of which are known to those skilled in the art, such as optically active tartaric, mandelic, cholic, 0,0-di-p-toluoyl tartaric, 0,0-di-benzoyl tartaric acids or other acids conventionally employed for this purpose. Spontaneous resolution can also be considered a means for separating the optically active isomers.

The potential of a product as a β-adrenergic blocking agent conventionally is evaluated by the protocol which was employed to assess the β-blocking properties of the novel compounds of this invention. The protocol employed comprises intravenous administration of graded doses of the selected compound to rats which then are challenged with a standard dose of isoproterenol, a product known to be a β-stimulant.

The clinical application of β-adrenergic blocking agents is well known to physicians. Uses for the novel products of this invention include treatment of angina pectoris, use in hypertension with or without other hypotensive drugs, control of tachycardia or cardiac arrhythmias due to excess catecholamines. In view of the considerable amount of literature that has accumulated concerning the use of β-adrenergic blocking agents, physicians would employ the products of this invention in any of the known conditions where a β-blocker is needed, such as in the management of the angina pectoris.

The products can be prepared in pharmaceutical formulations suitable for oral or parenteral administration preferably in the form of tablets, solutoins, suspensions or emulsions using well known techniques and excipients, diluents, lubricants, and the like. Dosage units of from about 1 mg. to about 40 mgs. can be provided for the symptomatic adjustment of dosage by the physician depending upon the age and condition of the patient.

The novel pyrazine products, I, of this invention advantageously can be prepared by the synthesis schematically illustrated below:

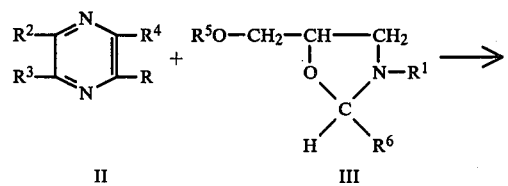

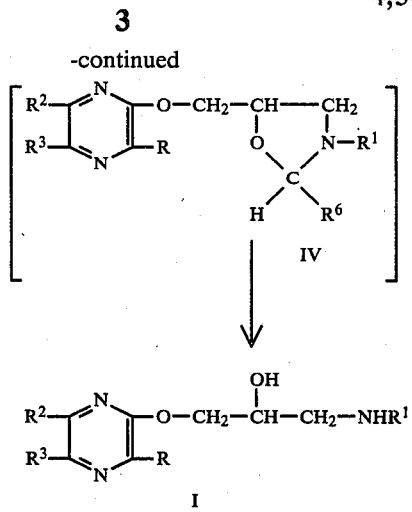

$$\downarrow$$

The pyrazine compound II is reacted with the oxazolidine, III, to give the oxazolidine adduct, IV, which when treated with mineral acid provides, the desired end product, I.

When $R^4$ in the pyrazine, II, is chloro or bromo, this compound is reacted with an oxazolidine, III, wherein $R^5$ is hydrogen. The reaction is carried out in the presence of a strong base and preferably at ambient temperature although the reaction mixture either can be heated up to reflux or cooled to 0° C. A solvent for the reactants is desirable and any conventional solvent can be employed for this purpose, suitable ones being lower alkanols or polar aprotic solvents such as dimethylformamide (DMF), dimethyl sulfoxide (DMSO), tetrahydrofuran (THF), hexamethylphosphoramide (HMP), and the like. The readily available and relatively inexpensive tert-butanol has been found to be a quite suitable, general purpose solvent for these intermediates. Strong bases that are recommended for use in the reaction are alkali metal alkoxides or alkali metal hydroxides, preferably the sodium or potassium alkoxides or hydroxides or sodium hydride. When the S-isomer of the oxazolidine is employed in the reaction one obtains product I in its sinister configuration. When the oxazolidine employed is not optically active, then the end product is obtained as a racemic mixture which can be separated by any of the conventional methods employed for this purpose.

When $R^4$ is the pyrazine starting material, II, represents a hydroxyl group then $R^5$ in the oxazolidine is a sulfonyl group. These reagents are coupled advantageously by combining the reactants in the presence of a strong base and a solvent, such as those described above, to form the intermediate IV which upon treatment with mineral acid provides the desired product I. Heating the reaction mixture up to the reflux temperature can be employed if desired and any of the usual organic solvents can be used especially selected from those identified above. When the oxazolidine reagent, III, is the optically active compound in the sinister configuration then the end product I is obtained in its sinister configuration also. Racemic III provides the end product I in its racemic form also which can be separated, if desired, by any of the conventional methods employed for this purpose.

When end product I in the form of the free base is obtained as an oil, crystalline material can be prepared by forming a salt thereof by known methods. Suitable salts are those formed with mineral acids or organic acids such as, for example, the hydrochloride salt, the sulfate salt, the hydrogen maleate salt, or other desired mineral or organic acid salt.

PREPARATION OF THE OXAZOLIDINE STARTING SUBSTANCES, III

The oxazolidine reagent, III, either as a racemic mixture or as the S-isomer can be prepared by published procedures by reacting 1,2-dihydroxy-3-substituted aminopropane or a 1-sulfonyloxy-2-hydroxy-3-substituted aminopropane with an aldehyde, $R^6CHO$, to provide the oxazolidine of structure III. When the S-isomer of the aminoalkanols are employed in the preparation of the oxazolidine it is obtained in its sinister configuration whereas racemic starting materials give racemic oxazolidines which themselves can be resolved into their optically active components. The aldehyde used in the preparation of the oxazolidine is not critical as any aldehyde can be used in the formation of the cyclic structure which subsequently is cleaved by acid hydrolysis to remove the $$-\underset{\underset{R^6}{|}}{C}H-$$

grouping provided by the aldehyde. For practical purposes, any commercially available and inexpensive aldehyde can be employed and among these there can be mentioned aliphatic aldehydes, alicyclic, aromatic or heterocyclic aldehydes such as formaldehyde, lower alkyl aldehydes, benzaldehyde, phenyl-lower alkyl aldehydes, and the like, the phenyl moiety of either of the latter aldehydes optionally having one or more similar or dissimilar substituents selected from halogen, lower alkyl, haloalkyl, amino, acylamino, mono- or dialkylamino, nitro, alkoxy, phenalkoxy, haloalkoxy, and hydroxy, a heterocyclic aldehyde optionally having substituents as halogen, lower alkyl, phenalkyl and the like. Among the many aldehydes that can be employed there can be mentioned formaldehyde, acetaldehyde, propionaldehyde, butyraldehyde, phenylacetaldehyde, anisaldehyde, benzaldehyde, mesitaldehyde, tolualdehyde, furfural and the like.

As mentioned above, $R^5$ can be hydrogen or an alkyl-, aryl-, or aralkyl-sulfonate. Again the particular sulfonyl group is not critical as any sulfonyl substituent that replaces the hydrogen of the 1-hydroxyl group of the 1,2-dihydroxy-3-substituted aminopropane or that replaces the hydrogen of the 5-hydroxyl group of the 5-hydroxymethyloxazolidine will activate these former hydroxyl substituents. For practical purposes, commercially available and inexpensive sulfonyl halides would be employed for this purpose and these would fall into the class of alkylsulfonyl halides and benzenesulfonyl halides wherein the benzene moiety can optionally be substituted with one or more similar or dissimilar substituents selected from lower alkyl, lower alkoxy, halo, amino, and nitro substituents. Among the commercially available sulfonyl halides that can be employed for this purpose there can be mentioned methanesulfonyl chloride, benzenesulfonyl chloride, nitrobenzenesulfonyl fluoride, trichlorobenzenesulfonyl chloride, tribromobenenesulfonyl chloride, fluorobenzenesulfonyl chloride, 4-chloro-2-(or 3)-nitrobenzenesulfonyl chloride, hexadecanesulfonyl chloride, 2-mesitylenesulfonyl chloride, methoxybenzenesulfonyl chloride and the like.

While many oxazolidine compounds of structure III are known compounds, the following procedures provide illustrative methods that are representative of feasible means for making those compounds that are not readily available commercially or which may be novel members required to introduce the desired 3-amino-2-hydroxypropoxy substituent in the 2-position of end product I.

METHOD 1-A: PREPARATION OF A 5-HYDROXYMETHYL-2-$R^6$-3-$R^1$-OXAZOLIDINE

PREPARATION 1:
S-3-(1-methyl-2-phenethyl)-5-hydroxymethyloxazolidine

Step A:
S-1,2-dihydroxy-3-(1-methyl-2-phenethylamino)propane

A mixture of 1-methyl-2-phenethylamine (0.513 mole), methanol (150 ml.) and 5% palladium-on-carbon (1.0 g.) is shaken in a hydrogenation bomb under three atmospheres hydrogen pressure. A solution of D-glyceraldehyde (15 g.) in methanol (60 ml.) is added over a one hour period during hyrogenation. After the addition, the mixture is shaken for an additional 15 hours. The catalyst is removed by filtration and the solvent evaporated in vacuo yielding S-1,2-dihydroxy-3-(1-methyl-2-phenthylamino)propane.

by replacing the 1-methyl-2-phenethylamine employed in Step A by an equivalent quantity of 1-methyl-2-(2-indolyl)ethylamine and following substantially the same procedure described in Step A, there is obtained S-1,2-dihydroxy-3-[1-methyl-2-(2-indolyl)ethylamino]propane.

Step B:
S-3-(1-methyl-2-phenethyl)-5-hydroxymethyloxazolidine

A mixture of S-1,2-dihydroxy-3-(1-methyl-2-phenethylamino)propane (0.2 mole), aqueous formaldehyde (20 ml. of 37% solution) and benzene (80 ml.) is heated under reflux with continuous removal of water for two hours. The solvent then is evaporated in vacuo (15 mm. pressure) providing S-3-(1-methyl-2-phenethyl)-5-hydroxymethyloxazolidine.

When an S-1-sulfonyloxy-2-hydroxy-3-(1-methyl-2-phenethylamino) propane is reacted with formaldehyde by the procedure described in Step B there is obtained S-3-(1-methyl-2-phenethyl)-5-hydroxymethyl-OXAZOLIDINE.

METHOD 1-B: PREPARATION OF A 5-SULFONYLOXYMETHYL-2-$R^6$-3-$R^1$-OXAZOLIDINE

Preparation 2: Preparation of S-3-(1-methyl-2-phenethyl)-5-(benzenesulfonyloxymethyl)oxazolidine To a solution of S-3-(1-methyl-2-phenethyl)-5-hydroxymethyloxazolidine (10 mmole), prepared as described in Procedure 1, Steps A and B, in pyridine (3 ml.) there is added benzenesulfonyl chloride (10 mmole) and the mixture stirred for about 1 hour at 25° C. Ether (20 ml.) is added whereupon S-3-(1-methyl-2-phenethyl)-5-(benzenesulfonyloxymethyl)oxazolidine hydrochloride is precipitated, removed by filtration and washed well with ether and dried in vacuo at 40° C.

Any of the needed oxazolidine reactants, structure III, can be made by Preparations 1 and 2 by replacing the 1-methyl-2-phenethylamine in Procedure 1, Step A by a required amine to yield the —$NHR^1$ substituent and reacting the dihydroxy-propylamine thus formed with any aldehyde of structure $R^6CHO$ to provide the 5-hydroxymethyl oxazolidine. This product then can conveniently be converted to the 5-sulfonyloxymethyloxazolidine by reaction with any sulfonyl chloride as described in Preparation 2. Representative oxazolidines that can be made by these procedures are identified in Table I.

TABLE I $R^1NH_2$ + D(orDL)glyceraldehyde +

Preparation 1-A conditions ⟶

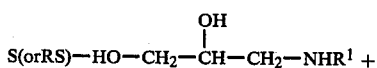

$R^6CHO$ + Preparation 1-B conditions ⟶

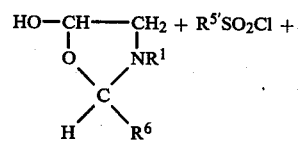

Preparation 2 conditions ⟶ 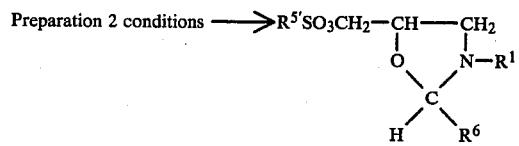

| Preparation No. | $R^1$ | $R^6$ | $R^{5'}$ |
|---|---|---|---|
| 3 | 1-methyl-2-(3-indolyl)ethyl | H | phenyl |
| 4 | Tert.-butyl | phenyl | p-tolyl |
| 5 | Tert.-butyl | H | p-tolyl |
| 6 | Tert.-butyl | H | p-bromophenyl |
| 7 | i-propyl | H | phenyl |
| 8 | 2,2-dimethylpropyl | H | methyl |
| 9 | 1,1-dimethyl-2-hydroxyethyl | H | p-chlorophenyl |
| 10 | 1,1-dimethyl-2-phenethyl | H | phenyl |
| 11 | 1,1-dimethyl-2-(2-indolyl)ethyl | H | p-tolyl |
| 12 | 2,2-dimethyl-2-(3-indolyl)ethyl | H | phenyl |

PREPARATION OF THE PYRAZINE STARTING SUBSTANCES, II

Many pyrazine starting substances of structure II have been described in the literature, any of which can be reacted with the appropriate oxazolidine (III) as discussed above to give the desired end product I. Some representative methods that can be employed for making any desired pyrazine that may not be readily available commercially are depicted below along with one or more examples to provide information concerning the working conditions suitable for carrying out each procedure.

METHOD 2: PREPARATION OF 2-R⁴-3-R-5-R³-6-R²-PYRAZINES

ROUTE I

Particularly Suitable When
R is alkyl, phenyl, substituted phenyl, benzyl, substituted benzyl, or cycloalkyl
R³ is hydrogen, alkyl, cycloalkyl, phenyl, or substituted phenyl and
R² is hydrogen, alkyl, cycloalkyl or phenyl

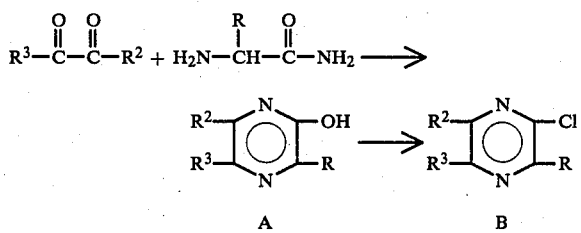

The following reaction is typical for the above sequence:

PREPARATION 13: 2-Chloro-3-p-methoxyphenylpyrazine

Step A: 2-Hydroxy-3-p-methoxyphenylpyrazine p-Methoxyphenyl glycinamide (0.10 mole) in 125 ml. methanol cooled to −30° C. is treated with a solution of 19.3 g. (0.10 ml.) of 30% glyoxal in 25 ml. methanol also precooled to −30° C. The mixture is stirred and added dropwise during 15–30 minutes to 10 ml. (0.125 mole) of 12.5 N aqueous sodium hydroxide, the temperature of the reaction mixture being held at −20° to 15° C. during this addition. The mixture is refrigerated 1–2 hours at −10° C., then 1 hour at −2° to 3° C., whereupon there is added 12 N HCl followed by 5 g. solid sodium bicarbonate to neutralize any excess acid. The solution then is evaporated to dryness and the residue extracted with chloroform. The extracts are evaporated and the product crystallized from a suitable solvent mixture, i.e. chloroform-methanol to give 2-hydroxy-3-p-methoxyphenylpyrazine.

Step B: 2-chloro-3-p-methoxyphenylpyrazine

The 2-hydroxy-3-p-methoxyphenylpyrazine is refluxed (120°–130° C.) with excess phosphorus oxychloride under stirring for 3–5 hours. The solution is evaporated to dryness at 50° C. in vacuo, cooled, ice is added, then treated with 10% sodium hydroxide solution, extracted with a suitable solvent such as diethyl ether, the ethereal solution washed with water and evaporated. The crude product is crystallized from a suitable solvent such as ethanol to give 2-chloro-3-p-methoxyphenylpyrazine.

The following procedure provides a feasible method for making the glycinamide reactant should this starting substance not be readily available.

Preparation 14: 2-Chloro-3-p-methylphenypyrazine

Step A: p-Methylphenylglycinamide p-Methylphenylglycine is dissolved in excess 6 N HCl and evaporated to dryness. The residue in the cold is dissolved in excess thionyl chloride and after standing at 20° C. for 1–2 hours is evaporated to dryness and the acid chloride hydrochloride is treated with aqueous ammonia for several hours to give 3-p-methylphenyl-glycinamide which is crystallized from a suitable solvent such as ethanol.

Step B: 2-Hydroxy-3-p-methylphenylpyrazine

By replacing the p-methoxyphenyl glycinamide employed in Procedure 13, A by an equivalent quantity of p-methylphenylglycinamide and following substantially the same procedure as described in Procedure 13, A there is obtained 2-hydroxy-3-p-methylphenylpyrazine.

Step C: 2-chloro-3-p-methylphenylpyrazine

By replacing the 2-hydroxy-3-phenylpyrazine employed in Procedure 13, B by an equivalent quantity of 2-hydroxy-3-p-methylphenylpyrazine and following substantially the same procedure as described in Procedure 13, B there is obtained 2-chloro-3-p-methylphenylpyrazine.

Preparation 15: 2-Chloro-3-cyclopentylpyrazine

By replacing the p-methylphenylglycine employed in Procedure 14, Step A by an equivalent quantity of cyclopentylglycine, there is obtained cyclopentylglycinamide. Substituting this cyclopentylglycinamide for that employed in Procedure 13 and following the methods described in Steps A and B of Procedure 13, there is obtained in Step A 2-hydroxy-3-cyclopentylpyrazine and in Step B 2-chloro-3-cyclopentylpyrazine.

Similarly, by replacing the p-methylphenylglycine in Step A of Procedure 14 by
16: p-nitrophenylglycine
17: p-aminophenylgylcine
and in each instance following the methods described in Steps A–C of Procedure 14, there is obtained, respectively Preparation 16:
Step B: 2-Hydroxy-3-p-nitrophenylpyrazine
Step C: 2-Chloro-3-p-nitrophenylpyrazine
Preparation 17:
Step B: 2-Hydroxy-3-p-aminophenylpyrazine
Step C: 2-Chloro-3-p-aminophenylpyrazine Additional pyrazines (II) that are advantageously prepared by Route I are identified in Table II werein the variable substituents R³, R², and R in the glyoxal (or α, β-diketone), glycinamide and in the pyrazines A and B are the groups identified in the table.

TABLE II

| Preparation No. | R³ | R² | R |
|---|---|---|---|
| 18 | methyl | H | methyl |
| 19 | methyl | methyl | methyl |
| 20 | phenyl | H | methyl |
| 21 | phenyl | methyl | propyl |
|  | methyl | phenyl | propyl |
| 22 | methyl | methyl | phenyl |
| 23 | H | H | p-hydroxyphenyl |
| 24 | H | H | p-methoxyphenyl |
| 25 | H | H | p-chlorophenyl |
| 26 | methyl | H | p-hydroxbenzyl |
| 27 | methyl | methyl | p-hydroxybenzyl |
| 28 | H | H | cyclohexyl |
| 29 | H | H | benzyl |
| 30 | phenyl | phenyl | benzyl |
| 31 | phenyl | H | benzyl |
| 32 | p-methylphenyl | H | phenyl |
| 33 | p-methoxyphenyl | H | phenyl |
| 34 | p-chlorophenyl | H | phenyl |
| 35 | p-nitrophenyl | H | phenyl |
| 36 | o-hydroxyphenyl | H | phenyl |
| 37 | m-hydroxyphenyl | H | phenyl |
| 38 | p-hydroxyphenyl | H | phenyl |

TABLE II-continued

| Preparation No. | R³ | R² | R |
|---|---|---|---|
| 39 | cyclohexyl | H | benzyl |
| 40 | cyclopentyl | H | benzyl |
| 41 | cyclohexyl | cyclohexyl | phenyl |
| 42 | pyridyl | pyridyl | methyl |

ROUTE II

Particularly suitable when

R is alkoxy, phenoxy (or substituted), benzyloxy (or substituted), or N-heterocyclic R² is H or alkoxy and wherein R²=R³=alkyl or phenyl

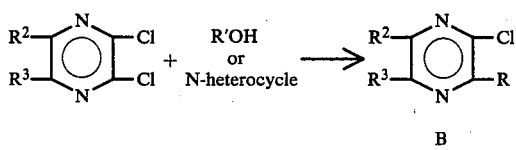

The following reactions are typical for the above sequence:

Preparation 43: 2-Chloro-3-methoxypyrazine

A mixture of 0.1 mole of 2,3-dichloropyrazine and 2.3 g. (0.1 mole) of sodium in 160 ml. of anhydrous methanol is refluxed 5–10 hours, and poured into water. The product is extracted with ether or chloroform and recrystallized from a suitable solvent such as ethanol to give pure 2-chloro-3-methoxypyrazine.

Preparation 44: 2-Chloro-3-phenoxypyrazine

A suspension of 0.1 mole of sodium phenoxide and 0.1 mole, 2,3-dichloropyrazine is refluxed 10–20 hours. The cooled mixture is extracted with diethyl ether, washed with cold 2 N sodium hydroxide solution, dried, and evaporated to give 2-chloro-3-phenoxypyrazine.

Preparation 45: 2-Chloro-3-benzyloxypyrazine

Sodium hydride (0.10 mole) is added to 0.10 mole of benzyl alcohol in 100 ml. dry benzene and the mixture is refluxed 1–2 hours. The cooled solution is treated with 0.10 mole of 2,3-dichloropyrazine in 100 ml. of benzene. The mixture is refluxed for 20–60 hours, cooled, washed with water, dried, and evaporated and the product distilled in vacuo to give 2-chloro-3-benzyloxypyrazine.

Preparation 46: 2-Chloro-3-morpholinopyrazine

A mixture of 2,3-dichloropyrazine (5 g., 0.034 mmole), morpholine (5.8 g., 0.067 mmole), and 50 ml. of dimethylformamide are heatd at 90°–120° C. for 6–14 hours, in an atmosphere of nitrogen. The reaction mixture is cooled and evaporated to dryness at a water-bath temperature of 55° C. A chloroform solution of the residue is extracted twice with 0.1 M sodium hydroxide, dried over magnesium sulfate and evaporated to leave the product.

Other 2-chloro-3-(N-hetero)pyrazines that are advantageously prepared by Route II, Preparation 46 are identified in Table III wherein 2,3-dichloropyrazine is reacted with the N-heterocycle identified in column 2 which displaces the 3-chloro by the radical identified in column 3.

TABLE III

| Preparation No. | N-heterocycle | R |
|---|---|---|
| 47 | pyrrole | pyrrolidinyl |
| 48 | piperidine | piperidino |
| 49 | hexahydroazepine | hexahydroazepinyl |
| 50 | pyrazole | pyrazolyl |
| 51 | imidazole | imidazolyl |
| 52 | triazole | triazolyl |
| 53 | thiomorpholine | thiomorpholino |

By replacing the 2,3-dichloropyrazine employed in Preparation 46 by

54: 2,3-dichloro-5,6-dimethylpyrazine and

55: 2,3-dibromo(or dichloro)-5,6-diphenylpyrazine there is obtained, respectively:

Preparation 54: 2-chloro-3-morpholino-5,6-dimethylpyrazine and

Preparation 55: 2-bromo(or chloro)-3-morpholino-5,6-diphenylpyrazine.

A 2-chloropyrazine described in the prior literature that is a useful intermediate is 2-Chloro-3-methoxymethyl-6-methoxypyrazine.

ROUTE III

Particularly suitable when

R is alkyl or phenyl and

R³ is alkyl or phenyl (or substituted), cycloalkyl, N-heterocyclic

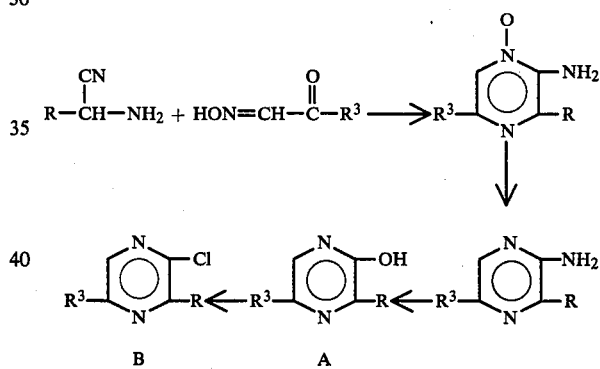

The reaction conditions for preparing the 2-hydroxypyrazine A are provided in detail by Sharp et al in J. Chem. Soc., 1951, 932–934, which is incorporated herein by reference.

Preparation 56: 2-Chloro-3,5-dimethylpyrazine

These workers described the preparation of 2-hydroxy-3,5-dimethylpyrazine which can be treated with phosphorus oxychloride by the method described in Preparation 13, Step B, to provide the desired 2-chloro-3,5-dimethylpyrazine.

Sharp et al, supra, describe the preparation of 2-amino-3-methyl-5-ethylpyrazine 1-oxide, 2-amino-3-phenyl-5-methylpyrazine 1-oxide and 2-amino-3-methyl-5-phenylpyrazine 1-oxide each of which can be converted by the methods described in the J. Chem. Soc. paper to the 2-hydroxy-3-methyl-5-ethylpyrazine, 2-hydroxy-3-phenyl-5-methylpyrazine, and 2-hydroxy-3-methyl-5-phenylpyrazine.

These compounds, in turn, can be reacted with phosphorus oxychloride by Preparation 13, Step B, method to give Preparation 57: 2-chloro-3-methyl-5-ethylpyrazine
Preparation 58: 2-chloro-3-phenyl-5-methylpyrazine
Preparation 59: 2-chloro-3-methyl-5-phenylpyrazine.

Other pyrazines advantageously prepared by Route III are identified in Table IV wherein the variable substituents R and $R^3$ in the oxime, nitrile, 2-aminopyrazine-1-oxide, 2-aminopyrazine and the pyrazines A and B are identified in the table.

TABLE IV

| Preparation No. | R | $R^3$ |
|---|---|---|
| 60 | methyl | phenyl |
| 61 | methyl | p-chlorophenyl |
| 62 | methyl | p-bromophenyl |
| 63 | methyl | methyl |
| 64 | phenyl | p-methoxy-phenyl |
| 65 | methyl | p-nitrophenyl |
| 66 | methyl | p-dimethylaminophenyl |
| 67 | methyl | cyclohexyl |
| 68 | methyl | 4-pyridyl |
| 69 | phenyl | 3-pyridyl |

ROUTE IV

Particularly suitable when
R is alkyl, phenyl, or cycloalkyl
$R^2$ is alkyl, phenyl, or cycloalkyl

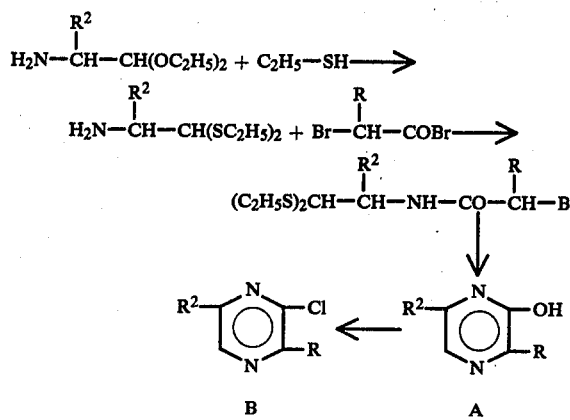

The procedural details for preparing 2-hydroxypyrazines (A) by this method are provided in a paper by Baxter et al, J. Chem. Soc., 1947, 370-372, which discussion is included herein by reference.

Preparation 70: 2-Chloro-3,6-dimethylpyrazine

The 2-hydroxy-3,6-dimethylpyrazine disclosed by Baxter et al can be reacted with phosphorus oxychloride by the method described in Preparation 13, Step B, to provide 2-chloro-3,6-dimethylpyrazine.

Preparation 71: 2-Chloro-3-phenyl-6-methylpyrazine

By employing α-bromo-α-phenylacetyl bromide (prepared by treating α-bromo-α-phenylacetic acid with $PBr_3$) in place of the 2-bromopropionyl bromide used by Baxter et al, supra, and following his method as depicted above, there is obtained 2-hydroxy-3-phenyl-6-methylpyrazine which when treated with phosphorus oxychloride by the method described in Example 13, Step B, 2-chloro-3-phenyl-6-methylpyrazine is obtained.

Varying the R and $R^2$ substituents in the starting materials other desired pyrazines A and B can be made particularly those identified in the heading of Route IV.

ROUTE V

Particularly suitable when
R is alkoxy, phenoxy (or substituted), benzyloxy (or substituted) or N-heterocyclic
$R^3$ is alkyl, alkoxy, phenyl

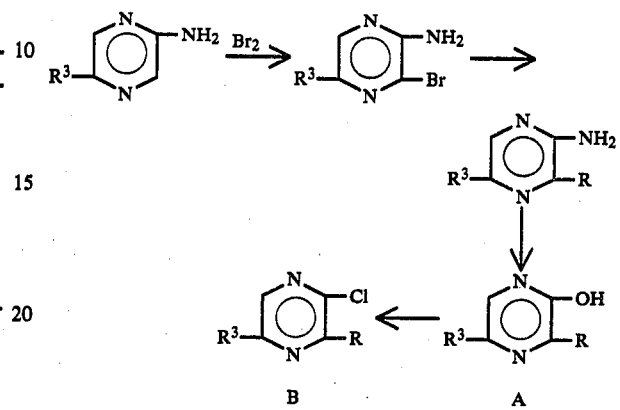

The following reactions are typical for the above sequence:

Preparation 72:
2-Chloro-3-n-propoxy-5-methylpyrazine

Step A: 2-Amino-3-bromo-5-methylpyrazine

To acetic acid (1500 ml.), 2-amino-5-methylpyrazine (1 mole) and 326.5 g. sodium acetate trihydrate are slowly added 1.1 mole bromine in 180 ml. acetic acid at 2° C. in the absence of light. The mixture is stirred about 15 hours at 20° C., stripped of acetic acid in vacuo, poured into ice, made alkaline with sodium hydroxide, filtered, and residue extracted with ether, the extract stripped and the 2-amino-3-bromo-5-methylpyrazine crystallized from a suitable solvent.

Step B: 2-Chloro-3-n-propoxy-5-methylpyrazine

By replacing the 2,3-dichloropyrazine and anhydrous methanol used in Preparation 43 by equivalent quantities of the product of Step A and n-propanol and following the method described in Preparation 43, 2-amino-3-n-propoxy-5-methylpyrazine is obtained. The 2-amino group can be converted to the 2-hydroxy by the method described by Sharp et al, ibid., (see Route III) which when treated with phosphorus oxychloride by the method of Preparation 13, Step B, provides 2-chloro-3-n-propoxy-5-methylpyrazine.

Preparation 73: 2-Chloro-3-phenoxy-5-ethylpyrazine

2-Amino-5-ethylpyrazine is brominated as described in Preparation 72, Step A, to provide 2-amino-3-bromo-5-ethylpyrazine. By replacing the 2,3-dichloropyrazine used in Preparation 44 by an equivalent quantity of 2-amino-3-bromo-5-ethylpyrazine and following substantially the same method, there is obtained 2-amino-3-phenoxy-5-ethylpyrazine. The 2-amino group is converted to the 2-hydroxy by the method described by Sharp et al, ibid., (see Route III) which when treated with phosphorus oxychloride by Preparation 13, Step B method, there is obtained 2-chloro-3-phenoxy-5-ethylpyrazine.

Preparation 74: 2-Chloro-3-benzyloxy-5,6-dimethylpyrazine

The known 2-amino-5,6-dimethylpyrazine can be brominated by Preparation 72, Step A method, and then reacted with benzyl alcohol by Preparation 45 method to provide 2-amino-3-benzyloxy-5,6-dimethylpyrazine. The 2-amino group is converted to the 2-hydroxy by the method described by Sharp et al, ibid., (see Route III) which when treated with phosphorus oxychloride by Preparation 13, Step B method, there is obtained 2-chloro-3-benzyloxy-5,6-dimethylpyrazine.

Preparation 75: 2-Chloro-3-morpholino-5-phenylpyrazine

2-Amino-5-phenylpyrazine is brominated as described in Preparation 72, Step A, to provide 2-amino-3-bromo-5-phenylpyrazine. By employing an equivalent quantity of this pyrazine for the 2,3-dichloropyrazine in Preparation 46 and following substantially the method described therein, 2-amino-3-morpholino-5-phenylpyrazine is obtained. The 2-amino group is converted to the 2-hydroxy by the method described by Sharp et al, ibid., (see Route III) which when treated with phosphorus oxychloride by Preparation 13, Step B method, there is obtained 2-chloro-3-morpholino-5-phenylpyrazine.

By following the procedure of Preparation 75 and employing a 2-aminopyrazine having the 5-$R^3$ substituent identified in column 2 and the N-heterocycle in column 3 the pyrazines A and B having the $R^3$ and R substituents identified in Table V are obtained.

TABLE V

| Preparation No. | $R^3$ | Heterocyclic Reactant | R |
|---|---|---|---|
| 76 | methoxy | piperidine | piperidino |
| 77 | methyl | hexahydroazepine | hexahydroazepinyl |
| 78 | phenyl | imidazole | imidazolyl |
| 79 | ethyl | thiomorpholine | thiomorpholino |
| 80 | methyl | triazole | triazolyl |

ROUTE VI

Particularly suitable when
R is alkoxy, phenoxy (or substituted), benzyloxy (or substituted) or N-heterocyclic The following reactions are typical for this sequence:

Preparation 81: 2-Chloro-3-butoxy-6-methoxypyrazine

Step A: 2-Chloro-6-methoxypyrazine 4-oxide

Hydrogen peroxide (1.5 ml. of 30%) is added to a solution of 10 mmole of 2-chloro-6-methoxypyrazine in 5 ml. acetic acid. The solution is heated at 60°–75° C. for 10–15 hours. The solution is concentrated to quarter volume, diluted with water and extracted with chloroform, washed, dried and evaporated to give 2-chloro-6-methoxypyrazine 4-oxide which may be crystallized from a suitable solvent such as ethanol.

Step B: 2-Amino-6-methoxypyrazine 4-oxide

2-Chloro-6-methoxypyrazine 4-oxide is treated with an excess of ammonium hydroxide in an autoclave at 150° C. for 14 hours. The reaction mixture is cooled and evaporated to dryness to give the crude product which may be used in the next step as is.

Step C: 2-Amino-3-chloro-6-methoxypyrazine

A suspension of 2-amino-6-methoxypyrazine 4-oxide in freshly distilled phosphorus oxychloride is refluxed for one hour. Thin layer chromatography indicates that the starting material is no longer present. The excess of phosphorus oxychloride is removed in vacuo and the residue is treated with crushed ice. After decomposition is complete the solution is made alkaline with 10% sodium hydroxide and extracted with chloroform. The chloroform extracts are washed with water, dried over sodium sulfate and evaporated to give the product which may be recrystallized from a suitable solvent such as ethanol.

Step D: 2-Amino-3-butoxy-6-methoxypyrazine

By replacing the pyrazine and methanol reactants in Preparation 43 by equivalent quantities of 2-amino-3-chloro-6-methoxypyrazine and butanol, respectively, and following substantially the same procedure there is obtained 2-amino-3-butoxy-6-methoxypyrazine.

Replacing the butanol in the above step by another alkanol as methanol, ethanol, propanol and the like, there is obtained the 2-amino-3-R-6-methoxypyrazine wherein R is methoxy, ethoxy, propoxy and the like.

Step E: 2-Chloro-3-butoxy-6-methoxypyrazine

The 2-amino substituent in the product of Step D is converted to the 2-hydroxy by reacting a solution of the

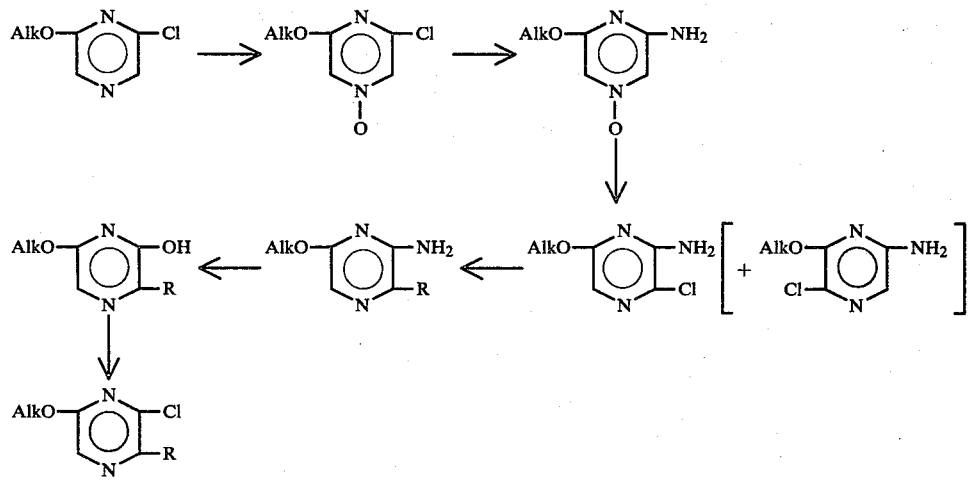

product of Step D in 6 M sulfuric acid at 0°–5° C. with a slight excess of sodium nitrite in water, adding the sodium nitrite solution at such a rate the temperature of the reaction mixture does not rise above about 5° C. After standing about 45 minutes at 0°–5° C. a little urea is added to destroy excess nitrous acid and the mixture is treated with sodium hydroxide until strongly basic. The reaction mixture is warmed to 60° C. for an hour, then adjusted to pH 8.5, concentrated to a third of its original volume, and cooled in a refrigerator overnight. The product is separated by filtration, dried in vacuo, recrystallized from a suitable solvent yielding 2-hydroxy-3-butoxy-6-methoxypyrazine. Treatment of this compound with phosphorus oxychloride by the method of Preparation 13, Step B, gives 2-chloro-3-butoxy-6-methoxypyrazine.

The other 2-amino-3-alkoxy-6methoxypyrazines (described following Step D) when substituted in Step E procedure give Preparation 82: 2-chloro-3,6-dimethoxypyrazine Preparation 83: 2-chloro-3-ethoxy-6-methoxypyrazine and Preparation 84: 2-chloro-3-propoxy-6-methoxypyrazine.

Preparation 85: 2-Chloro-3-phenoxy-6-methoxypyrazine

Step A: 2-Amino-3-phenoxy-6-methoxypyrazine

By replacing the 2,3-dichloropyrazine in Preparation 44 by an equivalent amount of 2-amino-3-chloro-6-methoxypyrazine and following substantially the same procedure there is obtained 2-amino-3-phenoxy-6-methoxypyrazine.

Step B: 2-Chloro-3-phenoxy-6-methoxypyrazine

The 2-amino substituent of Step A product when treated with sodium nitrite as described in Step E of Preparation 81 is converted to the 2-hydroxy group. Treatment of the 2-hydroxy-3-phenoxy-6-methoxypyrazine with phosphorus oxychloride by the method of Preparation 13, Step B, gives 2-chloro-3-phenoxy-6-methoxypyrazine.

Preparation 86: 2-Chloro-3-morpholino-6-methoxypyrazine

Step A: 2-Amino-3-morpholino-6-methoxypyrazine

By replacing the 2,3-dichloropyrazine used in Preparation 46 by an equivalent quantity of 2-amino-3-chloro-6-methoxypryazine and following substantially the same procedure there is obtained 2-amino-3-morpholino-6-methoxypyrazine.

Step B: 2-Chloro-3-morpholino-6-methoxypyrazine

The 2-amino substituent of Step A product when treated with sodium nitrite as described in Step E of Preparation 81 is converted to the 2-hydroxy group. Treatment of the 2-hydroxy-3-morpholino-6-methopxypyrazine with phosphorus oxychloride by Preparation 13, Step B method, gives 2-chloro-3-morpholino-6-methoxypyrazine.

Reaction of any of the other N-heterocycles with 2-amino-3-chloro-6-methoxypyrazine by the method of Preparation 86, Step A, followed by the methods of Step B gives the corresponding 2-chloro-3-(N-heterocyclic)-6-methoxypyrazine.

ROUTE VII

Particularly suitable when
R is alkyl or phenyl and
$R^3$ is alkoxy, phenoxy (or substituted), benzyloxy (or substituted) or N-heterocyclic

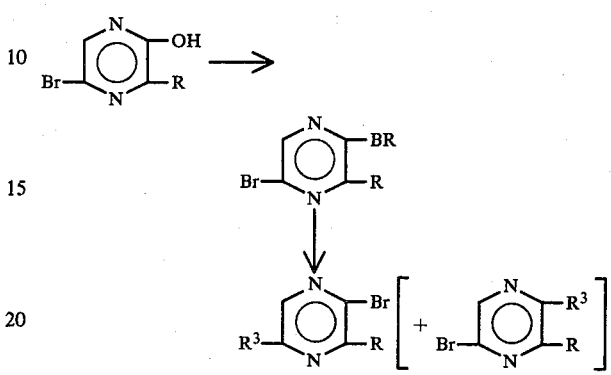

The following reactions are typical for the above sequence:

Preparation 87: 2-Bromo-3-methyl-5-methoxypyrazine

Step A: 2,5-Dibromo-3-methylpyrazine

A mixture of 2-hydroxy-3-methyl-5-bromopyrazine and phosphorus oxychloride is heated at about 175° C. for several hours with constant stirring. After hydrolysis of the solution on ice the crude product is extracted with ether and distilled. The distillate is refluxed with phosphorus tribromide for several hours and, after cooling, the solution is hydrolyzed on ice and the product extracted with ether, the ether removed in vacuo to give 2,5-dibromo-3-methylpyrazine.

Step B: 2-Bromo-3-methyl-5-methoxypyrazine

By replacing the 2,3-dichloropyrazine used in Preparation 43 by an equivalent quantity of 2,5-dibromo-3-methylpyrazine and following substantially the same procedure, there is obtained a major quantity of 2-bromo-3-methyl-5-methoxypyrazine and a small amount of 2-methoxy-3-methyl-5-bromopyrazine, which products can be separated by column chromatography on silica gel.

Preparation 88: 2-Bromo-3-phenyl-5-phenoxypyrazine

Step A: 2,5-Dibromo-3-phenylpyrazine

By replacing the 2-hydroxy-3-methyl-5-bromopyrazine used in Step A of Preparation 87 by an equivalent quantity of 2-hydroxy-3-phenyl-5-bromopyrazine and following substantially the same procedure there is obtained 2,5-dibromo-3-phenylpyrazine.

Step B: 2-Bromo-3-phenyl-5-phenoxypyrazine

By replacing the 2,3-dichloropyrazine in Preparation 44 by an equivalent quantity of 2,5-dibromo-3-phenylpyrazine and following substantially the same procedure, there is obtained a major quantity of 2-bromo-3-phenyl-5-phenoxypyrazine and a smaller quantity of 2-phenoxy-3-phenyl-5-bromopyrazine, the products being separable by column chromatography on silica gel.

Preparation 89: 2-Bromo-3-ethyl-5-benzyloxypyrazine

Step A: 2,5-Dibromo-3-ethylpyrazine

By replacing the 2-hydroxy-3-methyl-5-bromopyrazine used in Step A of Preparation 87 by an equivalent quantity of 2-hydroxy-3-ethyl-5-bromopyrazine and following substantially the same procedure, there is obtained 2,5-dibromo-3-ethylpyrazine.

Step B: 2-Bromo-3-ethyl-5-benzyloxypyrazine

By replacing the 2,3-dichloropyrazine used in Preparation 45 by an equivalent quantity of 2,5-dibromo-3-ethylpyrazine and following substantially the same procedure, there is obtained a major quantity of 2-bromo-3-ethyl-5-benzyloxypyrazine and a smaller quantity of 2-benzyloxy-3-ethyl-5-bromopyrazine, which products can be separated by column chromatography on silica gel.

Preparation 90: 2-Bromo-3-isopropyl-5-morpholinopyrazine

Step A: 2,5-Dibromo-3-isopropylpyrazine

The compound is prepared by replacing the 2-hydroxy-3-phenyl-5-bromopyrazine used in Step A of Preparation 87 by an equivalent quantity of 2-hydroxy-3-isopropyl-5-bromopyrazine.

Step B: 2-Bromo-3-isopropyl-5-morpholinopyrazine

By replacing the 2,3-dichloropyrazine used in Preparation 46 by an equivalent quantity of 2,5-dibromo-3-isopropylpyrazine and following substantially the same procedure there is obtained a major quantity of 2-bromo-3-isopropyl-5-morpholinopyrazine and a small amount of 2-morpholino-3-isopropyl-5-bromopyrazine, which products can be separated by column chromatography on silica gel.

By replacing the morpholine employed in Step B of Preparation 90 by an equivalent quantity of any of the other N-heterocycles, there is obtained 2-bromo-3-isopropyl-5-(N-heterocycle)-pyrazine.

ROUTE VIII

Particularly suitable when
R is alkoxy, phenoxy (or substituted), benzyloxy (or substituted), or N-heterocyclic
$R^3$ is alkoxy, phenoxy (or substituted), benzyloxy (or substituted), or N-heterocyclic, amino or acylamino

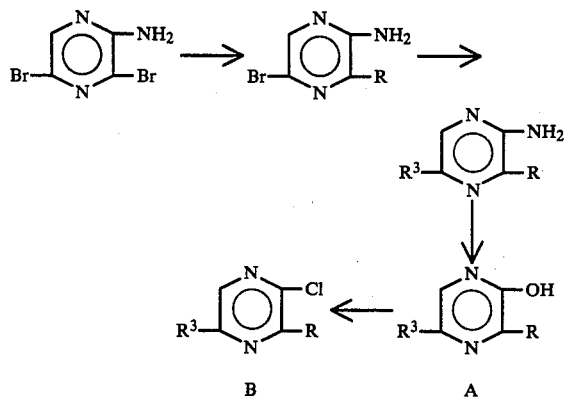

The following reactions are typical for the above sequence:

Preparation 91: 2-Chloro-3,5-dimethoxypyrazine

Step A: 2-Amino-3-methoxy-5-bromopyrazine

2-Amino-3,5-dibromopyrazine (7 g.) is boiled for about 9 hours with 0.65 g. sodium in 18.5 ml. methanol to give 2-amino-3-methoxy-5-bromopyrazine.

Step B: 2-Amino-3,5-dimethoxypyrazine

A mixture of 0.1 mole of 2-amino-3-methoxy-5-bromopyrazine and 0.1 mole of sodium in 160 ml. of anhydrous methanol is refluxed 5-10 hours and poured into water. The product is extracted with ether or chloroform and recrystallized from a suitable solvent such as ethanol to give 2-amino-3,5-dimethoxypyrazine.

Step C: 2-Hydroxy-3,5-dimethoxypyrazine

A solution of 2-amino-3,5-dimethoxypyrazine (0.02 mole) in 300 ml. of 6 M sulfuric acid at 0°-5° C. is treated with 0.022 mole sodium nitrite in 25 ml. of water at such a rate to insure that the temperature of the reaction mixture does not rise above 5° C. After standing 45 minutes at 0°-5° C., a little urea is added to destroy excess nitrous acid and the mixture then is treated with sodium hydroxide solution until strongly basic. The reaction mixture is warmed to 60° C. for one hour and then brought to pH 8.5. The mixture is concentrated to a third of the original volume and cooled in the refrigerator overnight. The product is separated by filtration and dried in vacuo, recrystallized from a suitable solvent to give 2-hydroxy-3,5-dimethoxypyrazine.

Step D: 2-Chloro-3,5-dimethoxypyrazine

Treatment of the above-obtained 2-hydroxy-3,5-dimethoxypyrazine with phosphorus oxychloride by the method described in Preparation 13, Step B, gives 2-chloro-3,5-dimethoxypyrazine.

Replacement of the methanol employed in Steps A and B of Preparation 91 with an equivalent quantity of ethanol, propanol, butanol or other lower alkanol and following substantially the same methods described in the preceding procedure there is obtained the corresponding 2-chloro-5-(ethoxy, propoxy, butoxy)-5-methoxypyrazine.

Preparation 92: 2-Chloro-3,5-dimorpholinopyrazine

Step A: 2-Amino-3-morpholino-5-bromopyrazine

2-Amino-3,5-dibromopyrazine is reacted with morpholine at 130° C. under pressure yielding 2-amino-3-morpholino-5-bromopyrazine.

Step B: 2-Amino-3,5-dimorpholinopyrazine

A mixture of the above-obtained 2-amino-3-morpholino-5-bromopyrazine (0.04 mmole), morpholine (0.07 mmole) and 50 ml. of dimethylformamide are heated at 100°-140° C. for about 3 to 5 days in an atmosphere of nitrogen. The reaction mixture is cooled and evaporated to dryness at a water bath temperature of 55° C. A chloroform solution of the residue is extracted twice with 0.1 M sodium hydroxide, dried over magnesium sulfate and evaporated to leave 2-amino-3,5-dimorpholinopyrazine.

Step C: 2-Chloro-3,5-dimorpholinopyrazine

This product is obtained by treating the 2-amino-3,5-dimorpholinopyrazine with sodium nitrite by the method described in the preceding procedure, Step C, and then with phosphorus oxychloride by the method described in Preparation 13, Step B.

Preparation 93:
2-Chloro-3-morpholino-5-aminopyrazine

Step A: 2-Hydroxy-3-morpholino-5-bromopyrazine

2-Amino-3-morpholino-5-bromopyrazine (see Preparation 92, Step A) is treated with sodium nitrite by the method described in Preparation 91, Step C, to give 2-hydroxy-3-morpholino-5-bromopyrazine.

Step B: 2-Hydroxy-3-morpholino-5-aminopyrazine

A mixture of 2-hydroxy-3-morpholino-5-bromopyrazine (1g.) in 100 ml. of concentrated ammonium hydroxide is heated overnight at 100°-140° C. in a sealed tube to give 2-hydroxy-3-morpholino-5-aminopyrazine.

Step C: 2-Chloro-3-morpholino-5-aminopyrazine

Treatment of the 2-hydroxy-3-morpholino-5-aminopyrazine with phosphorus oxychloride by the method described in Preparation 13, Step B, gives the desired 2-chloro-3-morpholino-5-aminopyrazine.

Preparation 94:
2-Chloro-3-morpholino-5-phenoxypyrazine

Step A: 2-Amino-3-morpholino-5-phenoxypyrazine

A suspension of 0.1 mole of sodium phenoxide and 0.1 mole of 2-amino-3-morpholino-5-bromopyrazine is refluxed 10-20 hours. The cooled mixture is extracted with diethyl ether, washed with cold 2 N sodium hydroxide solution, dried and evaporated to give 2-amino-3-morpholino-5-phenoxypyrazine.

Step B: 2-Chloro-3-morpholino-5-phenoxypyrazine

Upon treatment of the 2-amino-3-morpholino-5-phenoxypyrazine with nitrous acid by the method described in Preparation 91, Step C, there is obtained the corresponding 2-hydroxy-compound which when treated with phosphorus oxychloride by the method described in Preparation 13, Step B, gives the desired 2-chloro-3-morpholino-5-phenoxypyrazine.

Preparation 95:
2-Chloro-3-morpholino-5-benzyloxypyrazine

Step A: 2-Amino-3-morpholino-5-benzyloxypyrazine

Sodium hydride (0.1 mole) is added to benzyl alcohol (0.1 mole) in 100 ml. dry benzene and the mixture is refluxed one to two hours. The cooled solution is treated with 0.1 mole of 2-amino-3-morpholino-5-bromopyrazine in 100 ml. of benzene and the resulting mixture refluxed for 20-60 hours whereupon it is cooled, washed with water, dried and evaporated to give 2-amino-3-morpholino-5-benzyloxypyrazine.

Step B: 2-Chloro-3-morpholino-5-benzyloxypyrazine

Upon treatment of the 2-amino-3-morpholino-5-benzyloxypyrazine with nitrous acid by the method described in Preparation 91, Step C, there is obtained the corresponding 2-hydroxy-compound which upon treatment with phosphorus oxychloride by the method described in Preparation 13, Step B, gives 2-chloro-3-morpholino-5-benzyloxypyrazine.

PREPARATION OF THE PYRAZINE END PRODUCTS, I

The following examples will illustrate representative products of this invention by the reaction of a 2-chloropyrazine with a 5-hydroxymethyloxazolidine or by the reaction of a 2-hydroxypyrazine with a 5-sulfonyloxymethyloxazolidine compound. A representative example providing typical reaction conditions for each of these methods follows. While the table identifying representative end products shows their preparation by reacting a 2-chloropyrazine with a 5-hydroxymethyloxazolidine, it is to be understood that the corresponding 2-hydroxypyrazine (the preparation of which is also included in the preceding discussion) can as well be reacted with the 5-sulfonyloxymethyloxazolidine to provide the same end product and preparation by this alternative method is to be understood as being included for each product identified.

EXAMPLE 1

S-(−)-2-(3-tert-butylamino-2-hydroxypropoxy)-3-phenylpyrazine hydrogen maleate

A mixture of S-2-phenyl-3-tert-butyl-5-hydroxymethyloxazolidine (540 mg., 2 mmoles plus 15% excess), 2-chloro-3-phenylpyrazine (382 mg., 2 mmoles) and potassium tert-butoxide (224 mg., 2 mmoles) in tert-butanol (3 ml.) are permitted to stand 6 days at ambient temperature. The solution then is evaporated to dryness, the residue treated with N hydrochloric acid (4 ml.) and stirred 75 minutes at 55°-65° C. The mixture is cooled, extracted with diethyl ether, and the aqueous layer treated with excess potassium carbonate until the solution is strongly basic. The mixture is extracted with diethyl ether and evaporation of the ether extracts gives 557 mg. of a light yellow oil. Thin layer chromatography (TLC) showed the presence of a single compound which gave an $R_f$ value that differed from that of starting material. The oil is dissolved in ethyl acetate (10 ml.) and treated with maleic acid (215 mg.) in ethyl acetate (9 ml.) to give 570 mg. of S-(−)-2-(3-tert-butylamino-2-hydroxypropoxy)-3-phenylpyrazine hydrogen maleate, m.p. 136.0°-138.5° C. Recrystallization from a mixture of methanol and ethyl acetate and drying in vacuo provides 485 mg. of product, m.p. 137.5°-139.0° C., $[\alpha]_D^{25} -5.205$ (C=3%, CH$_3$OH).

Analysis calculated for $C_{17}H_{22}O_2N_3 \cdot C_4H_4O_4$: C, 60.42; H, 6.52; N, 10.07; Found: C, 60.10; H, 6.68; N, 10.25.

EXAMPLE 2

S-(−)-2-(3-tert-butylamino-2-hydroxypropoxy)-3-n-propylpyrazine hydrogen maleate S-3-tert-butyl-5-(p-toluenesulfonyloxymethyl)oxazolidine (Preparation 5) (10 mmole) are dissolved in benzene (12 ml.) and tetrahydrofuran (0.9 ml.). The sodium salt of 2-hydroxy-3-n-propylpyrazine (10 mmole) is added and the mixture refluxed for about 20 hours. The reaction mixture then is extracted with 3 10-ml. portions of 1 N hydrochloric acid and the aqueous layer then made alkaline with ammonia and extracted with 3 10-ml. portions of benzene. The combined benzene extracts are dried and evaporated to give S-(−)-2-(3-tert-butylamino-2-hydroxypropoxy)-3-n-propylpyrazine. This product is converted to the hydrogen maleate salt by treatment with maleic acid in tetrahydrofuran by substantially the same procedure described in Example 1.

Any other 5-R$^5$-oxymethyl-2-R$^6$-3-R$^1$-oxazolidine starting substance (III) can be substituted for the oxazolidines employed in Examples 1 and 2 for reaction with the desired pyrazine (II) to provide end product I.

The following table identifies representative novel S-2-(3-$R^1$-amino-2-hydroxypropoxy)-3-R,5-$R^3$-6-$R^2$-pyrazine compounds falling within the scope of this invention which are prepared by the method of either Example 1 or 2.

TABLE VI

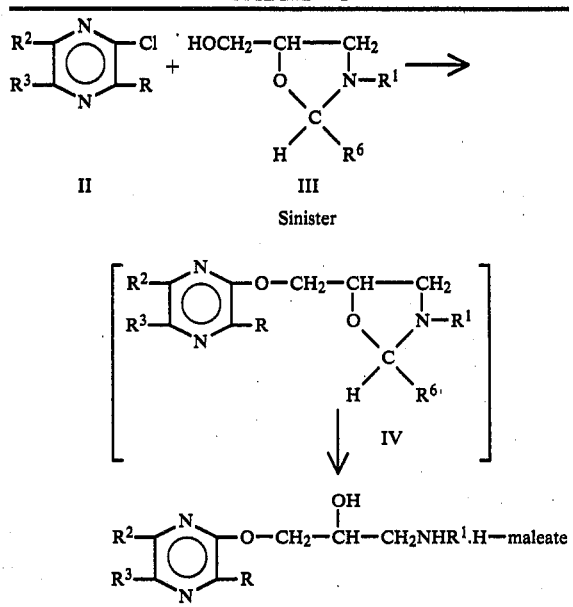

Sinister

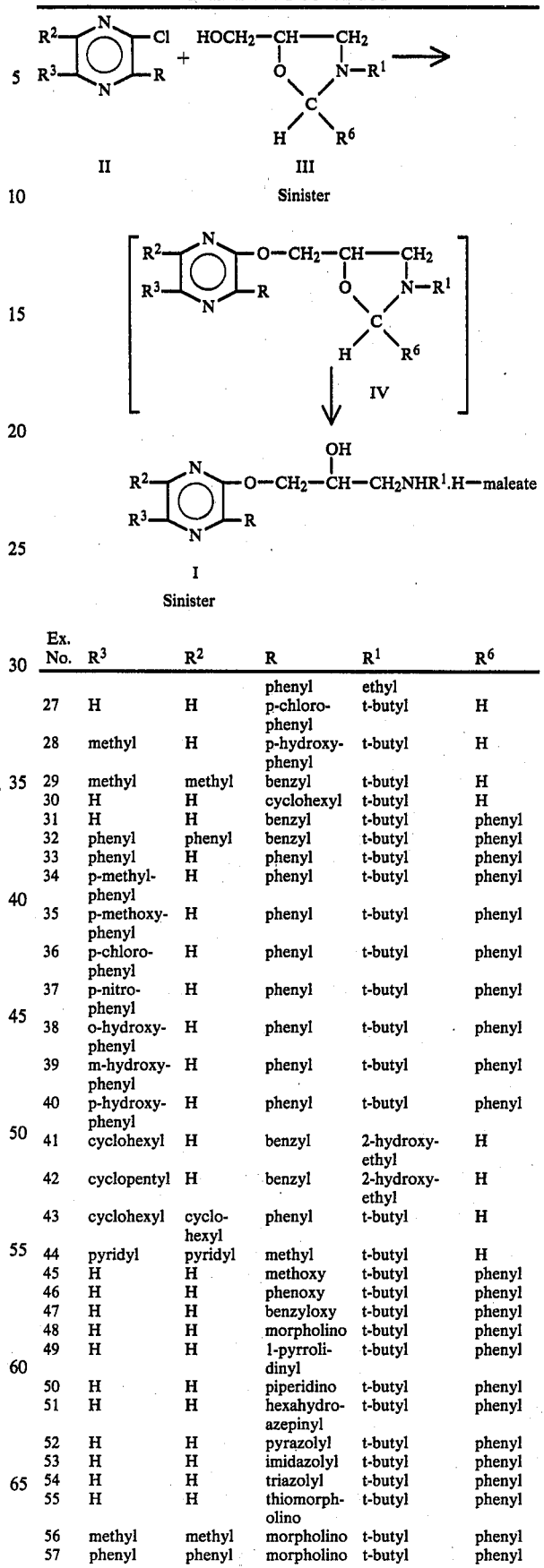

Sinister

| Ex. No. | $R^3$ | $R^2$ | R | $R^1$ | $R^6$ |
|---|---|---|---|---|---|
| 3 | H | H | propyl | t-butyl | H |
| 4 | H | H | methyl | t-butyl | i-propyl |
| 5 | H | H | ethyl | 1-methyl-2-phenethyl | H |
| 6 | H | H | i-propyl | 1-methyl-2-(3-indolyl)ethyl | H |
| 7 | H | H | phenyl | t-butyl | H |
| 8 | H | H | phenyl | i-propyl | phenyl |
| 9 | H | H | methyl | 3-(2,2-dimethyl)propyl | phenyl |
| 10 | H | H | phenyl | 1,1-dimethyl-2-hydroxyethyl | phenyl |
| 11 | H | H | ethyl | 1,1-dimethyl-2-phenethyl | phenyl |
| 12 | H | H | ethyl | 1,1-dimethyl-2-(3-indolyl)-ethyl | phenyl |
| 13 | H | H | ethyl | 2,2-dimethyl-2-(3-indolyl)-ethyl | phenyl |
| 14 | H | H | p-methoxyphenyl | t-butyl | phenyl |
| 15 | H | H | p-methylphenyl | t-butyl | phenyl |
| 16 | H | H | cyclopentyl | 1,1-dimethyl-propargyl | H |
| 17 | H | H | p-nitrophenyl | t-butyl | phenyl |
| 18 | H | H | p-aminophenyl | t-butyl | phenyl |
| 19 | methyl | H | methyl | t-butyl | phenyl |
| 20 | methyl | methyl | methyl | t-butyl | phenyl |
| 21 | phenyl | H | methyl | t-butyl | phenyl |
| 22 | phenyl | methyl | propyl | t-butyl | phenyl |
| 23 | methyl | phenyl | propyl | t-butyl | phenyl |
| 24 | methyl | methyl | phenyl | t-butyl | phenyl |
| 25 | H | H | p-hydroxyphenyl | i-propyl | H |
| 26 | H | H | p-methoxyphenyl | 2-hydroxyethyl | H |
| 27 | H | H | p-chlorophenyl | t-butyl | H |
| 28 | methyl | H | p-hydroxyphenyl | t-butyl | H |
| 29 | methyl | methyl | benzyl | t-butyl | H |
| 30 | H | H | cyclohexyl | t-butyl | H |
| 31 | H | H | benzyl | t-butyl | phenyl |
| 32 | phenyl | phenyl | benzyl | t-butyl | phenyl |
| 33 | phenyl | H | phenyl | t-butyl | phenyl |
| 34 | p-methylphenyl | H | phenyl | t-butyl | phenyl |
| 35 | p-methoxyphenyl | H | phenyl | t-butyl | phenyl |
| 36 | p-chlorophenyl | H | phenyl | t-butyl | phenyl |
| 37 | p-nitrophenyl | H | phenyl | t-butyl | phenyl |
| 38 | o-hydroxyphenyl | H | phenyl | t-butyl | phenyl |
| 39 | m-hydroxyphenyl | H | phenyl | t-butyl | phenyl |
| 40 | p-hydroxyphenyl | H | phenyl | t-butyl | phenyl |
| 41 | cyclohexyl | H | benzyl | 2-hydroxyethyl | H |
| 42 | cyclopentyl | H | benzyl | 2-hydroxyethyl | H |
| 43 | cyclohexyl | cyclohexyl | phenyl | t-butyl | H |
| 44 | pyridyl | pyridyl | methyl | t-butyl | H |
| 45 | H | H | methoxy | t-butyl | phenyl |
| 46 | H | H | phenoxy | t-butyl | phenyl |
| 47 | H | H | benzyloxy | t-butyl | phenyl |
| 48 | H | H | morpholino | t-butyl | phenyl |
| 49 | H | H | 1-pyrrolidinyl | t-butyl | phenyl |
| 50 | H | H | piperidino | t-butyl | phenyl |
| 51 | H | H | hexahydroazepinyl | t-butyl | phenyl |
| 52 | H | H | pyrazolyl | t-butyl | phenyl |
| 53 | H | H | imidazolyl | t-butyl | phenyl |
| 54 | H | H | triazolyl | t-butyl | phenyl |
| 55 | H | H | thiomorpholino | t-butyl | phenyl |
| 56 | methyl | methyl | morpholino | t-butyl | phenyl |
| 57 | phenyl | phenyl | morpholino | t-butyl | phenyl |

TABLE VI-continued

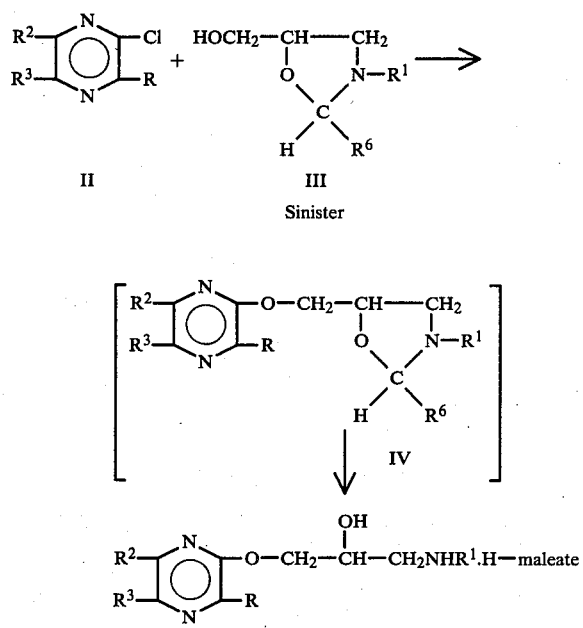

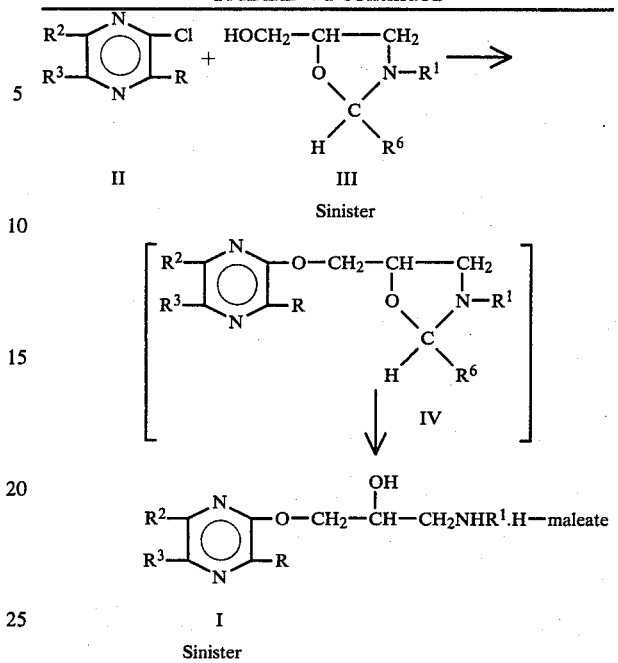

| Ex. No. | R³ | R² | R | R¹ | R⁶ |
|---|---|---|---|---|---|
| 58 | methyl | H | methyl | t-butyl | phenyl |
| 59 | ethyl | H | methyl | t-butyl | phenyl |
| 60 | methyl | H | phenyl | t-butyl | phenyl |
| 61 | phenyl | H | methyl | t-butyl | phenyl |
| 62 | p-chlorophenyl | H | methyl | t-butyl | phenyl |
| 63 | p-bromophenyl | H | methyl | t-butyl | phenyl |
| 64 | methyl | H | methyl | t-butyl | phenyl |
| 65 | methoxy | H | phenyl | t-butyl | phenyl |
| 66 | p-nitrophenyl | H | methyl | t-butyl | phenyl |
| 67 | p-dimethylaminophenyl | H | methyl | t-butyl | phenyl |
| 68 | cyclohexyl | H | methyl | t-butyl | phenyl |
| 69 | 4-pyridyl | H | methyl | t-butyl | phenyl |
| 70 | 3-pyridyl | H | phenyl | t-butyl | phenyl |
| 71 | H | methyl | methyl | t-butyl | phenyl |
| 72 | H | methyl | phenyl | t-butyl | phenyl |
| 73 | methyl | H | propoxy | t-butyl | phenyl |
| 74 | ethyl | H | phenoxy | t-butyl | phenyl |
| 75 | methyl | methyl | benzyloxy | t-butyl | phenyl |
| 76 | phenyl | H | morpholino | t-butyl | phenyl |
| 77 | methoxy | H | piperidino | t-butyl | phenyl |
| 78 | methyl | H | hexahydroazepinyl | t-butyl | phenyl |
| 79 | phenyl | H | imidazolyl | t-butyl | phenyl |
| 80 | ethyl | H | thiomorpholino | t-butyl | phenyl |
| 81 | methyl | H | triazolyl | t-butyl | phenyl |
| 82 | H | methoxy | butoxy | t-butyl | phenyl |
| 83 | H | methoxy | methoxy | t-butyl | phenyl |
| 84 | H | methoxy | ethoxy | t-butyl | phenyl |
| 85 | H | methoxy | propoxy | t-butyl | phenyl |
| 86 | H | methoxy | phenoxy | t-butyl | phenyl |
| 87 | H | methoxy | morpholino | t-butyl | phenyl |
| 88 | methoxy | H | methyl | t-butyl | phenyl |
| 89 | phenoxy | H | phenyl | t-butyl | phenyl |
| 90 | benzyloxy | H | ethyl | t-butyl | phenyl |
| 91 | morpholino | H | i-propyl | t-butyl | phenyl |
| 92 | methoxy | H | methoxy | t-butyl | phenyl |
| 93 | morpholino | H | morpholino | t-butyl | phenyl |
| 94 | amino | H | morpholino | t-butyl | phenyl |
| 95 | phenoxy | H | morpholino | t-butyl | phenyl |
| 96 | benzyloxy | H | morpholino | t-butyl | phenyl |

We claim:
1. A pyrazine compound having the structure

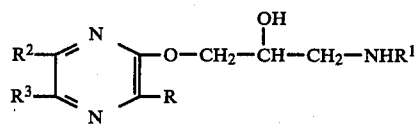

or a pharmacologically acceptable salt thereof wherein
R represents piperidino;
R¹ represents a straight or branched chain $C_{3-6}$alkyl, a straight or branched chain hydroxy substituted $C_{3-6}$alkyl, a straight or branched chain $C_{3-6}$alkinyl, phenyl-$C_{1-6}$alkyl or indolyl-$C_{1-6}$alkyl;
R² and R³ can represent the same or different substituents and represent hydrogen, $C_{1-3}$alkyl, $C_{5-7}$cycloalkyl, $C_{1-3}$alkoxy, phenoxy, phenyl, substituted phenyl wherein the substituent is $C_{1-3}$alkyl, $C_{1-3}$alkoxy, amino, acylamino, nitro or halo.

2. A pharmaceutical composition for use in hypertension in unit dosage form comprising a pyrazine of claim 1 and a carrier.

3. A pyrazine compound as claimed in claim 1 wherein R² and R³ are each hydrogen.

4. A pyrazine compound as claimed in claim 1 wherein R² and R³ are each hydrogen and R¹ is a straight or branched chain $C_{3-6}$alkyl.

5. A pyrazine compound as claimed in claim 4 wherein R¹ is tert-butyl.

6. A pyrazine compound as claimed in claim 1 wherein R² is hydrogen.

7. A pyrazine compound as claimed in claim 1 wherein R³ is hydrogen.

* * * * *